(12) United States Patent
Yahiaoui et al.

(10) Patent No.: US 7,045,559 B2
(45) Date of Patent: *May 16, 2006

(54) ELECTRICALLY CONDUCTIVE ADHESIVE HYDROGELS WITH SOLUBILIZER

(75) Inventors: Ali Yahiaoui, Roswell, GA (US); Caron Keller, McCammon, ID (US); Richard Arnold Borders, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/740,942

(22) Filed: Dec. 18, 2003

(65) Prior Publication Data

US 2005/0137276 A1 Jun. 23, 2005

(51) Int. Cl.
- *A61L 24/00* (2006.01)
- *C08F 2/46* (2006.01)

(52) U.S. Cl. .............. 523/111; 523/103; 523/105; 522/88; 522/87; 522/173; 522/175; 522/182; 522/180; 522/86; 525/937; 525/329.4; 525/936; 524/916; 524/831

(58) Field of Classification Search .............. 522/88, 522/87, 173, 175, 180, 182, 86; 523/103, 523/105, 111; 525/937, 329.4, 936; 524/916, 524/831

See application file for complete search history.

(56) References Cited

U.S. PATENT DOCUMENTS

| | | | |
|---|---|---|---|
| 4,391,278 A | 7/1983 | Cahalan et al. | |
| 4,524,087 A | 6/1985 | Engel | |
| 4,539,996 A | 9/1985 | Engel | |
| 4,554,924 A | 11/1985 | Engel | |
| 4,581,821 A | 4/1986 | Cahalan et al. | |
| 4,842,768 A | 6/1989 | Nakao et al. | |
| 4,848,353 A | 7/1989 | Engel | |
| 5,080,099 A | 1/1992 | Way et al. | |
| 5,124,076 A | 6/1992 | Smuckler | |
| 5,183,599 A | 2/1993 | Smuckler | |
| 5,264,249 A | 11/1993 | Perrault et al. | |
| 5,402,884 A | 4/1995 | Gilman et al. | |
| 5,800,685 A | 9/1998 | Perrault | |
| 6,038,464 A | 3/2000 | Axelgaard et al. | |
| 6,174,929 B1 * | 1/2001 | Hahnle et al. | ........... 521/64 |
| 6,197,173 B1 * | 3/2001 | Kirkpatrick | ........... 204/478 |
| 6,198,955 B1 | 3/2001 | Axelgaard et al. | |
| 6,229,062 B1 | 5/2001 | Mandell et al. | |
| 6,344,218 B1 | 2/2002 | Dodd et al. | |
| 6,347,246 B1 | 2/2002 | Perrault et al. | |
| 6,559,223 B1 * | 5/2003 | Green et al. | ........... 524/831 |
| 6,656,456 B1 | 12/2003 | Dodd et al. | |
| 2002/0026005 A1 | 2/2002 | Munro | |
| 2003/0031715 A1 | 2/2003 | Park et al. | |
| 2003/0054024 A1 | 3/2003 | Munro et al. | |
| 2004/0057986 A1 | 3/2004 | Merrigan et al. | |

FOREIGN PATENT DOCUMENTS

| | | |
|---|---|---|
| EP | 1245241 A1 | 10/2002 |
| EP | 1358894 A1 | 11/2003 |
| WO | WO 00/45864 | 8/2000 |
| WO | WO 00/66187 | 11/2000 |
| WO | WO 03/051408 | 6/2003 |
| WO | WO 03/089506 | 10/2003 |
| WO | WO 2004/029169 | 4/2004 |
| WO | WO 2004/052415 | 6/2004 |

OTHER PUBLICATIONS

McAdams, E., "Surface Biomedical Electrode Technology", *International Medical Device & Diagnostic Industry*, Sep./Oct. 1990, pp. 44-48.

Berner, G. et al., "Photoinitiators-An Overview", *Journal of Radiation Curing*, Apr. 1979, pp. 2-9.

Liu, YuYang et al., "Synthesis and characterization of pH- and temperature-sensitive hydrogel of N-isopropylacrylamide/cyclodextrin based copolymer", *Polymer*, vol. 43, No. 18, Aug. 2002, pp. 4997-5003.

* cited by examiner

*Primary Examiner*—Sanza L. McClendon
(74) *Attorney, Agent, or Firm*—William W. Letson; Scott B. Garrison

(57) ABSTRACT

A composition providing electrically conductive adhesive hydrogels suitable for use as skin contact adhesives and, particularly, suitable for use as an electrical interface for disposable medical devices. The present hydrogels provide for reduced skin irritation and/or malodor properties, hydrate a subject's skin, readily wet around a subject's skin surface hair, and protect against burning of a subject upon or due to electrical stimulation through the hydrogel. These hydrogels generally include a monomer, a first initiator, a solubilizer, and a cross-linking agent. The present hydrogels also desirably include a buffer system to help prevent discoloration of the hydrogels and/or hydrolysis of the hydrogels as well as to improve shelf-life. Other additives such as conductivity enhancers, pharmaceuticals, humectants, plasticizers, skin health agents, etc. may be added to the present hydrogels either before or after curing.

39 Claims, No Drawings

ELECTRICALLY CONDUCTIVE ADHESIVE HYDROGELS WITH SOLUBILIZER

BACKGROUND

At present, electrically conductive adhesive solid hydrogels and liquid gels are used in the medical device field to provide an electrical interface to the skin of a subject to couple electrical signals into and/or out of the subject (e.g., for diagnostic and/or monitoring uses) and/or to couple electrical stimulus into the subject (e.g., for treatment and/or preventative uses). However, the present hydrogels and liquid gels are inadequate in various aspects.

Prior hydrogels exhibit problems with their adhesive and/or cohesive strength in that they do not sufficiently adhere to the skin, they are insufficiently cohesive to allow for easy removal, and/or they are adherent to themselves such that they must be physically separated, as by a barrier film, to ensure separability (no straight face-to-face, gel-to-gel, configurations). See, e.g., Gilman, et al., U.S. Pat. No. 5,402,884 (a package system providing electrical communication between two hydrogel portions, but still requiring separation of the two hydrogel portions). Additional problems with prior hydrogels concern sufficiently hydrating the skin in contact with the hydrogel and, therefore, problems with sufficiently lowering the skin's electrical resistance thereby frequently resulting in heating to a point of burning the skin upon electrical stimulation. See, e.g., E. McAdams, "Surface Biomedical Electrode Technology," Int'l Med. Device & Diagnostic Indus. pp. 44–48 (September/October 1990).

Further problems with prior hydrogels include insufficiently wetting around skin hair and resultant problems with insufficiently contacting the skin. This leads to insufficient electrical contact thereby frequently resulting in decreased efficacy of defibrillation and increased incidences of heating to the point of burning the skin upon electrical stimulation and/or problems of requiring preparation of skin surfaces prior to use thereby resulting in slowing the speed of procedures. Further still, electrical pulses transmitted through prior hydrogels to a patient cause hydrolysis of the gel, and this problem is exacerbated with medical stimulation equipment used for defibrillation and/or cardiac pacing because these types of stimulation equipment usually deliver higher voltages and currents to the patient which increases the rate of hydrolysis. For example, defibrillation equipment typically delivers up to 5,000 volts to the patient at a maximum current of 60 amps, and cardiac pacing equipment commonly delivers up to 300 volts to the patient at a maximum current of 0.2 amps.

Yet another problem with prior hydrogels is that the hydrogels often have an unpleasant odor associated with them. Some prior hydrogels also exhibit properties that are irritating to the skin of a patient. Skin irritation issues often arise where polymerization of the functional monomer and/or other monomeric residues in the hydrogel is not complete. In some cases, other undesired monomeric residues are present and, over time after manufacture, may come in direct contact with the patient skin and thus may further cause skin irritation.

Liquid gels experience similar problems and have the additional problem of not retaining a set shape over time due to their fluidity which affects their ease of use and storability, and problems of requiring even more time for clean-up due to their lack of cohesive strength.

Therefore, a new hydrogel which is suitable for use in skin-contact and medical devices, and which addresses and resolves these problems is needed.

SUMMARY OF THE INVENTION

In response to the difficulties and problems discussed above a composition for an electrically conductive hydrogel has been developed. The composition includes a monomer, an initiator, a cross-linking agent, and a solubilizer. The composition may be characterized in that the solubilizer allows for a higher initiator concentration to be solubilized in the composition; and such that the composition has a higher polymerizing potential than a similar composition without the solubilizer. Further the composition may having a lower concentration of residual monomeric compounds present in the hydrogel than that of a similar hydrogel without the solubilizer.

Alternatively, a composition for an electrically conductive hydrogel may include an ionic monomer, a first initiator, a cross-linking agent, and a solubilizer, wherein the solubilizer is selected from the group consisting of cyclodextrin or cyclodextrin derivatives.

The compositions of the present invention may be incorporated in a number of products. One example is an electrode comprising an electrically conductive adhesive hydrogel formed from a composition having a monomer, a first initiator, a cross-linking agent, and a solubilizer. The composition may be characterized in that the solubilizer allows for a higher initiator concentration to be solubilized in the composition, such that the composition has a higher polymerizing potential than a similar composition without the solubilizer. The electrode may also have a lower concentration of residual monomeric compounds present in the hydrogel than that of a similar hydrogel without the solubilizer.

The invention will be more fully understood and further features and advantages will become apparent when reference is made to the following detailed description of exemplary aspects of the invention and the accompanying drawings.

DETAILED DESCRIPTION OF THE PRESENT INVENTION

The present invention relates to electrically conductive adhesive hydrogels and, more particularly, to electrically conductive adhesive hydrogels suitable for use as a skin-contacting electrical interface for medical devices.

Hydrogel precursors of the present invention may be used to form electrically conductive adhesive hydrogels which are suitable for use as skin-contact adhesives and are good electrical conductors suitable for use in disposable medical devices, for example. Desirable skin-contact adhesives are non-irritating, are sufficiently wet to substantially wet and adhere to skin, and are sufficiently cohesive to be readily removable. Such adhesives further would sufficiently contact and wet skin to allow passage of electrical current without substantially adversely affecting the hydrogel or skin.

A number of different hydrogel precursor formulations are commercially available, at least one of which includes an initiator to promote the polymerization of the monomers in the precursor. Many of the prior formulations exhibit undesirable properties including issues with skin irritation, odor, electrical conductivity, adhesiveness, and the like. It has been discovered that some of those problems are, in large part, the result of poor polymerization of the monomers in the hydrogel precursors. That is, the functional monomers and other monomeric residues in the hydrogel precursors are not fully polymerizing thereby leaving residual monomer and/or by-products, which can cause or result in the some of the above undesirable properties.

Conventional industrial polymerization processes seldom yield complete reactions and thus residual monomer remains. Therefore, whether or not an initiator was present in prior hydrogel precursors, polymerization of the monomers in the prior hydrogels frequently was not complete and residual functional monomer and other monomeric residues remained. As the presence of the residual functional monomer and/or other monomeric residues is believed to be a cause of malodor and/or may result in skin irritation, the presence of residual functional monomer and other monomeric residues is desirably avoided or minimized. For instance, it has been discovered that the presence of an acrylic type residual monomer, such as acrylic acid or methyl acrylate, in a hydrogel may lead to an odor issue and/or skin irritation.

The present hydrogels have unique and improved properties as compared to other conductive hydrogels. More particularly, the present polymerizing formulations or hydrogel precursors exhibit enhanced polymerization, thereby reducing the amount of residual functional monomer and/or other monomeric residues in the hydrogel which are unpolymerized and are thus available to cause or result in malodor of the resulting hydrogel and/or skin irritation of a subject.

It will be appreciated that while reference is generally made throughout this disclosure to a hydrogel, in addition to referring to the end product, the term hydrogel, also may refer to the polymerizing formulation or hydrogel precursor which is converted to a hydrogel upon exposure to certain conditions (e.g., UV curing, heat, etc.) as discussed elsewhere herein.

By the term "similar composition" what is meant is a composition which uses essentially the same manufacturing processes and materials as the inventive composition but in which the inventive item is lacking. According to *Webster's New Collegiate Dictionary* (1980), "similar" means 1) having characteristics in common; strictly comparable, 2) alike in substance or essentials; corresponding. Using this commonly accepted meaning of the word similar, this term means that all other conditions are essentially the same, within manufacturing tolerances, except for the inventive conditions mentioned.

At least one prior hydrogel composition (e.g., U.S. Pat. No. 5,800,685, the disclosure of which is incorporated herein in its entirety) is known to have included a monomer, a cross-linking agent, and an initiator. However, the types of initiator cited in the '685 patent have limited water solubility in the precursor described. Therefore, if a higher amount of initiator (i.e. above the solubility limit) is needed to achieve a more complete polymerization that is not possible with the teachings of the '685 patent. Thus, the '685 patent presents a situation where there may not have been enough initiator present in soluble form to fully polymerize the monomer. Alternatively, if a higher concentration of hydrophobic initiator was present, the hydrogel became cloudy due to phase separation as a result of solubility limits being reached and exceeded by the addition of the initiator.

It has been discovered that the addition of a solubilizer to a hydrogel precursor allows for enhanced polymerization of the monomer, thereby leading to a reduction in or the avoidance of the presence of residual functional monomer and/or other monomeric residue. Such a reduction can provide for the provision of certain properties or the reduction or elimination of other properties depending on the beginning monomers and initiators of the hydrogel. Specifically, where the polymerization process is enhanced by the inclusion of a solubilizer so as to allow a higher level of initiator to be included in the hydrogel precursor without the difficulties discussed above, the amount of residual functional monomer and/or other monomeric residue may be reduced or avoided, thereby reducing the odor of the resulting hydrogel as well as reducing the risk of skin irritation of a user.

The present hydrogels become more stable with an associated extension of their shelf life which is another advantage of the present hydrogels not observed in previous hydrogels. That is, the more complete the polymerization process the more stable the hydrogel is during storage. This stability and extended shelf life can provide for significant cost savings as fewer products will fail post-manufacturing. Additionally, the stability and extended shelf life are expected to contribute to a decrease in the chances of getting a failed or defective product in an emergency situation provided a non-expired product is selected.

It will be appreciated that certain of the suitable solubilizers (e.g., cyclodextrin, cyclodextrin derivatives, and the like) also may act as a complexing and stabilizing agent. Thus, even in those aspects of the present invention wherein the concentration of initiator in the hydrogel precursor is below the solubility limit, without the addition of a solubilizer, and the addition of solubilizer would heretofore have been considered unnecessary and non-beneficial, the addition of a solubilizer which is or acts as a complexing agent can reduce the volatility of certain molecules (typically those associated with malodor) in the hydrogel and thus reduce the odor of the hydrogel.

Additionally, suitable solubilizers may act as carriers for desired hydrophobic ingredients (e.g., lipids, vitamins, antioxidants, drugs, fragrance, and other skin care ingredients, etc.) to help solubilize them in water so as to allow them to become more homogeneously integrated within the hydrogel.

The use of a solubilizer as a complexing agent and/or a carrier as noted above may exist whether the initiator present in the hydrogel precursor is hydrophilic or hydrophobic. However, where a hydrophilic initiator is used, the complexing agent can act as a carrier for a hydrophobic agent such as a skin care ingredient (e.g., lipid, etc.). It will be further appreciated that a solubilizer can act as a complexing agent and/or a carrier regardless of the initiator concentration compared to its solubility limit in the hydrogel precursor.

As indicated above, while prior hydrogel precursors may have included a hydrophobic initiator, the inclusion of excess hydrophobic initiator (an amount above the solubility limit therefor in the hydrogel precursor) is generally not considered beneficial and, in fact, can be detrimental as it can cause cloudiness of the hydrogel or result in phase separation.

The present invention presents a solution to some of the problems associated with prior hydrogels as at least one aspect of the present invention provides for the inclusion of initiator in an amount above its unmodified solubility limit (the solubility limit of the initiator in a hydrogel precursor without the addition of a solubilizer), thereby allowing for enhanced polymerization of the functional monomer and other monomeric residue of the hydrogel precursor as compared to a similar composition without the solubilizer.

For example, where an initiator such as IRGACURE® 184 (available from Ciba Specialty Chemicals, Inc., Tarrytown, N.Y.) is present without a solubilizer, the solubility limit of the initiator in a particular hydrogel precursor may be about 0.15% by weight of the hydrogel precursor. The addition of IRGACURE® 184 in an amount above its solubility limit will result in super saturation causing or resulting in cloudiness and/or phase separation; however, polymerization will not be enhanced. The inclusion of a solubilizer such as cyclodextrin or a cyclodextrin derivative can raise the solubility level of the hydrophobic initiator in the hydrogel precursor and enhances the prospect of a more complete polymerization and formation of a more homogenous hydrogel.

The inclusion of a solubilizer and the ability to include a higher level of solubilized initiator can be significant in certain aspects of the present invention in view of the fact that the functional monomers received from suppliers generally contain a polymerization inhibitor such as monomethyl ether hydroquinone (MEHQ) which is added to the monomer by the manufacturer in order to prevent spontaneous polymerization of the monomer during shipping and/or storage. While the inhibitor makes the monomer more stable, the inhibitor also becomes problematic during the hydrogel manufacturing process. That is, the inhibitor hinders the polymerization process because it quenches radicals in the same manner as it inhibits spontaneous polymerization of the functional monomer during storage. In addition, oxygen dissolved during preparation of the monomer solution also can have an inhibitory effect on the overall polymerization process. Thus, the presence of an inhibitor (e.g., MEHQ) and oxygen in solution counteracts the initiator. Thereby, the initiator is desirably present in soluble form in an amount to overcome the inhibiting effect of all inhibitors, such as MEHQ, dissolved oxygen and other radical scavenging moieties, so that the polymerization reaction desirably may go to or near completion.

As will be appreciated where an amount of initiator which is in solution (rather than separated out because of over saturation) and thereby is capable of initiating polymerization is consumed or neutralized by an inhibitor less soluble initiator is available for polymerization of the monomer. Thus, it can be desirable to raise the amount of initiator which is in solution and therefore available for polymerization of the monomer.

Further, the inclusion of an initiator in an amount which exceeds its solubility limit in the aqueous environment of the hydrogel precursor is different than the inclusion of or the ability to include an initiator in an amount above its normal or unmodified solubility limit in the aqueous environment, but which is also at or below the modified or elevated solubility limit created by the addition of a solubilizer. That is, the inclusion of the solubilizer increases the amount of initiator which may be solubilized and thus is available to enhance the initiation process and counteract the radical quenching of the inhibitors, leaving a higher quantity of solubilized initiator available for polymerization of the functional monomer and/or other monomeric residues than would be present or available for polymerization in the absence of the solubilizer. Enhanced polymerization of the functional monomer and other monomeric residues (e.g., acrylic acid, methyl acrylate, etc.) in the hydrogel precursor can result in a reduction of the odor of the resulting hydrogel and the potential for irritation of the skin as compared to the hydrogel which would have been formed without the presence of the solubilizer.

Having generally described one aspect of the present invention, the disclosure herein shifts to a more detailed discussion thereof. Specifically, one aspect of the present invention is directed to an electrically conductive hydrogel having a monomer, an initiator, a cross-linking agent, and a solubilizer. As noted above, the solubilizer can enable enhancement of the polymerization of the functional monomer and other monomeric residues. In some aspects, the solubilizer provides for a higher soluble initiator concentration without experiencing the difficulties noted above. In others the solubilizer can act as a complexing agent to reduce odor of the hydrogel, and/or the solubilizer can act as a carrier for a hydrophobic ingredient (e.g., lipids, vitamins, anti-oxidants, drugs, fragrance, other skin care ingredients, and the like) to help homogeneously solubilize them in the hydrogel so their attributes may be taken advantage of.

Note that where the sole function of the addition or inclusion of a solubilizer in the present invention is to achieve or allow for the achievement of higher initiator solubility levels and the results thereof, the initiator is limited to hydrophobic initiators, as hydrophilic initiators generally will not present the same issues in the amounts of initiator contemplated by the present invention. The limitation to the use of a hydrophobic initiator applies where only one initiator is present. Where more than one initiator is present in the hydrogel and the sole function of the addition or inclusion of a solubilizer is to achieve or allow for the achievement of higher initiator solubility levels and the results thereof, then at least one of the initiators should be an initiator that has a solubility limit issue in the particular precursor. However, either hydrophilic or hydrophobic initiators can be used where a solubilizer is included for another purpose (e.g., as a complexing agent or carrier for other hydrophobic ingredients) or in addition to modifying or elevating solubility limit of an initiator in the hydrogel precursor.

With regard to the functional monomer, it is contemplated that the hydrogels may be formed from any suitable monomer. In at least one aspect of the present invention, the hydrogel may be formed by free radical polymerization in the presence of water. Initiation of the formation of the hydrogel may be begun by ultra-violet curing with an initiator and a multifunctional cross-linking agent. While only one initiator is necessary, the hydrogel precursors may contain one or more second initiators. The initiators can be photo-initiators or chemical initiators such as those activated by heat or by reduction/oxidation (redox) reactions.

While any suitable monomer is contemplated by the present invention, exemplary functional monomers include: N-vinyl pyrrolidone (NVP), hydroxyethyl methacrylate (HEMA), methacrylic acid (MA) or its salt, styrene sulfonic acid (SSA) or its salt, potassium sulfopropyl acrylate (KPSA), dimethyl acrylamide (DMA), dimethyl amino ethyl methacrylate (DMAEMA) or its quaternary salt derivative, acrylamido methyl propane sulfonic acid (AMPS) or its salt, and the combination of any of the above. Desirably, the hydrogels of the present invention are made from various classes of monomers including acrylates, vinyls, amides, esters, etc, of which can be electrically neutral, cationic or anionic. Combination of functional monomers also is possible to achieve desired physical, chemical mechanical and electrical properties. Compared to prior hydrogels, acrylate hydrogels (for example) of the present invention hydrate more efficiently and more sufficiently a subject's skin surface to which they are applied and, therefore, more efficiently and more sufficiently lower the skin surface's electrical resistance resulting in lower generation of heat and lower incidence of burning upon electrical stimulation. In addition, the present hydrogels more effectively wet around skin hair and, consequently, more sufficiently contact a subject's skin resulting in increased efficacy in procedures such as defibrillation as well as reduced heating and burning of skin surfaces and, generally require no preparation of the skin surface prior to use. Furthermore, the present hydrogels are self-preserving and are resistant to degradation upon exposure to radiation for sterilization purposes.

Generally, one aspect of the present hydrogel precursor includes between about 10 to about 80% by weight of the monomer, more desirably between about 40 to about 75% by weight of the monomer, and even more desirably between about 50 to about 75% by weight of the monomer.

Examples of specific cationic acrylates which the inventors have found commercially available are: acryloyloxyethyltrimethyl ammonium chloride which is readily available from CPS Chemical Co. (New Jersey) or Allied Colloid (U.K.); acryloyloxyethyltrimethyl ammonium methyl sulfate which is also available from CPS Chemical Co. or Allied Colloid; and, acrylamidopropyltrimethyl ammonium chloride, which is available from Stockhausen (Germany). The desired process for making hydrogels with these exemplary acrylates is described in detail below.

A cationic acrylate hydrogel suitable for the present invention will generally be somewhat clear in color, viscous, and tacky to the touch. The hydrogel tends to be sufficiently adhesive to a subject's skin, yet sufficiently cohesive to be easily removable from the subject's skin and separable from itself. As noted above, the hydrogels suitable for the present invention can be formed by in-situ free radical polymerization of a water soluble monomer in the presence of water, desirably by ultra-violet curing with at least one hydrophobic initiator, multi-functional cross-linking agent(s), and a solubilizer (e.g., cyclodextrin, etc.). For example, an appropriate acrylate monomer, water, optional additional conductor(s) (e.g., sodium chloride, potassium chloride, or other salts), hydrophobic initiator or catalyst (e.g., 1-hydroxycyclohexylphenol ketone, etc.), multi-functional cross-linker (e.g., methylene-bis-acrylamide, etc.), and solubilizer (e.g., cyclodextrin, etc.) are combined, placed in a mold, and exposed to an appropriate amount of ultra-violet radiation.

Examples of co-monomers which may be used with the present invention include co-monomers soluble in water and, even more desirably, include anionic co-monomers. The amount of co-monomer to be used may be in the range of about 5 to about 50% by weight, desirably about 10 to about 30% by weight, based on the amount of reactants used. Examples of suitable co-monomers include: unsaturated organic carboxylic acids such as acrylic acid, methacrylic acid, maleic acid, itaconic acid, and citraconic acid and salts thereof, unsaturated organic sulfonic acids such as styrene sulfonic acid, methallyl sulfonic acid, 2-sulfoethyl acrylate, 2-sulfoethyl methacrylate, 3-sulfopropyl acrylate, 3-sulfopropyl methacrylate, acrylamido-methylpropane sulfonic acid and salts thereof, N,N-dimethylacrylamide, vinyl acetate, other radically polymerizable ionic monomers containing a carbon-carbon double bond, and non-N-vinyl lactam co-monomers useful with N-vinyl lactam monomeric units such as N-vinyl-2-pyrrolidone, N-vinyl-2-valerolactam, N-vinyl-2-caprolactam, and mixtures thereof. Among the ionic monomers enumerated above, particularly desirable selections are 3-sulfopropylacrylate or methacrylate, and salts thereof. Examples of cations involved in the formation of such salts include sodium, potassium, lithium, and ammonium ions. Ionic monomers may be used singly or in a mixture of two or more monomers.

Any suitable solubilizer or combination of solubilizers is contemplated. The desirability of a specific solubilizer and/or the amount thereof which is included in hydrogel precursor may vary or depend in part on the other components and quantities thereof selected to make up the hydrogel precursor. Exemplary solubilizers include but are not limited to cyclodextrin, cyclodextrin derivatives, and hydrotropes. Specific exemplary cyclodextrin derivative solubilizers that are known to work in at least one aspect of the present invention include hydroxypropyl beta-cyclodextrin (HP-β-CD) (available from Cargill Dow, Minnetonka, Minn.), gamma cyclodextrin (γ-CD) (available from Wacker Biochem Corporation, Adrian, Mich.) and other polymerizable cyclodextrin derivatives such as methacryloyl cyclodextrin.

If a specific initiator is selected, then some solubilizers may be more desirable than others. That being said, it is contemplated that a solubilizer may be present in a positive amount up to about 20% by weight of the hydrogel precursor and, more desirably, between about 0.5% to about 5% by weight of the hydrogel precursor.

Present hydrogels may include a buffer system to help control the pH, prevent discoloration, and/or prevent breakdown due to an extended presence of water (i.e., hydrolysis). The use of a buffer system with the present hydrogel is desired to provide the hydrogel with a commercially suitable shelf-life (i.e., a shelf-life of over one year) without discoloration. Suitable buffers include but are not limited to sodium potassium tartarate, and/or sodium phosphate monobasic, both of which are commercially readily available from Aldrich Chemical Co., Inc., Milwaukee, Wis.

In addition, the use of buffers also helps to prevent electro-chemical burning of a subject by helping to prevent pH changes and/or shifts as a current is driven through a pair of hydrogel electrodes. Typically, in prior systems, as current is driven through a pair of hydrogel electrodes, one electrode becomes more acidic (i.e., its pH decreases) while the other electrode becomes more basic (i.e., its pH increases). This pH shifting problem is particularly prevalent if current is driven through such electrodes for a long period of time (e.g., over 1 hour), such as during a procedure wherein a patient's heart is being paced. The desired use of a buffer system as is suggested in the present invention helps safeguard against such pH changes as current is driven therethrough and thereby enables use of the electrodes made from the present hydrogel for longer periods (e.g., over 24 hours) without electro-chemical burning.

Therefore, it is desired that buffer be included to stabilize the resulting polymer, to avoid hydrolysis of the hydrogel, and to avoid pH shifts due to the passage of direct current through the hydrogel. Buffers help both to reduce or prevent corrosion of metal conductors and also are conductivity enhancers themselves. Some buffers prevent undesirable yellowing of the hydrogel. The present hydrogel may include sufficient buffer to maintain the pH of the hydrogel in a range of about 3 to about 8, and more desirably about 4 to about 6, but the pH may be adjusted as desired. In most aspects of the present invention, a buffer may be present in the hydrogel precursor in an amount up to about 10% by weight, and more desirably from about 0 to about 5% by weight of the hydrogel precursor.

Although a buffer also may be a conductivity enhancer, the quantities of the buffer and conductivity enhancers described herein are independent of one another. That is, if a particular hydrogel precursor is intended to include 1% by weight of a conductivity enhancer and 1% by weight of a buffer, the buffer which also may happen to be a conductivity enhancer can but generally will not count towards the amount of enhancer included.

The present invention also contemplates the inclusion of other additives, such as conductivity enhancers, pharmaceuticals, humectants, plasticizers, skin health agents, and the like. These other additives may be included either before or after a curing step. The appropriateness of such additives is generally dependent upon the intended end use of the particular hydrogel.

Any suitable additive or combination of additives such as those suggested above is contemplated. The specific additive and/or the amount thereof which is included may vary or depend in part on the other components and quantities thereof selected to make up the hydrogel. Exemplary skin health agents and/or skin care ingredients include but are not limited to vitamins (e.g., B, D, E, E acetate, etc.), antioxidants, chitosan, aloe Vera, hyaluronic acid (HA), heparin, chondroitin sulfate, dextran sulfate, and collagen IV. Still other exemplary additives may include but are not limited to anti-inflammation agents, anti-oxidants, aesthetic agents (e.g., color dyes to alter appearance of the hydrogels), or fragrances.

As noted above, any suitable conductivity enhancer is contemplated. The specific enhancer and/or the amount thereof which is included in the hydrogel may vary or depend in part on the other components, and quantities thereof selected to make up the hydrogel. Exemplary conductivity enhancers include but are not limited to salts such as potassium chloride, sodium chloride, potassium sulfate, and the like. These salts are desired inasmuch as human bodies use them for conduction. Additional examples of salts which may be appropriate are lithium chloride, lithium perchlorate, ammonium chloride, calcium chloride, and/or magnesium chloride. Other chloride salts, iodide salts, bromide salts, and/or halide salts also may be suitable.

Other salts, such as salts of weak organic acids or polymeric electrolytes may be desirable. These salts are compatible with human bodies and with the chemistry of the hydrogels of the present invention and may be used as conductivity enhancers where desired chloride salts might interfere (i.e., corrode) with aluminum and/or stainless steel metal components used to interface the hydrogel with medical equipment. Examples of salts which may be suitable, include sodium citrate or magnesium acetate.

Although use of a conductivity enhancer is optional, the amount of conductivity enhancer in a hydrogel of the present invention is desirably in the range of none to an amount which will enhance the conductivity of the hydrogel, and more desirably a conductivity enhancer will be present in an amount between about 0 to about 15% by weight of the hydrogel precursor and, even more desirably, less than about 5% by weight of the hydrogel precursor.

The addition of conductivity enhancers may be desired even though the hydrogel of the present invention is a polyelectrolyte ionically disassociated in water and, therefore, conductive. In utility, a lower specified quantity of polyelectrolyte (and thus a hydrogel having a correspondingly lower viscosity) may be desired in situations such as when the hydrogel must wet around chest hair. In such cases, the addition of a conductivity enhancer may be useful.

However, while the addition of a conductivity enhancer to a hydrogel or hydrogel precursor has generally been thought to provide for better electrical conductivity when compared to hydrogels without the added conductivity enhancer, it has been discovered that at least some aspects of the present invention which do not include an added conductivity enhancer demonstrate better in use conductivity as compared to those hydrogels which included a conductivity enhancer. For example, in certain instances, salts, despite being inherently electrically conductive because of their ionicity, may negatively yield undesirable effects such as the "salting out" effect which may result in phase separation and/or contribute to the reduced conductivity of certain formulations. This is especially true the longer the shelf life a hydrogel may be subjected to.

As indicated herein, a buffer and/or one or more of the optional polyelectrolyte additives (e.g., HA, chondroitin sulfate, phospholipids, etc.) may exhibit conductivity enhancing properties; however, the buffer and/or polyelectrolyte additives are not contemplated to be included in the determination of the amount of a conductivity enhancer in the hydrogel as the buffer and/or polyelectrolyte additives may not form a continuous path within the gel and between the gel and the skin.

As is mentioned above, initiators are used in the polymerization of the hydrogel precursors described herein. Examples of initiators which may be used include IRGACURE® 184 (1-hydroxycyclohexyl phenyl ketone), IRGACURE® 2959 (4-(2-hydroxyethoxy)phenyl-(2-hydroxy-2-methylpropyl)ketone)), and DAROCURE® 1173 α-hydroxy-α,α-dimethylacetophenone), all commercially available from Ciba Specialty Chemicals. These UV initiators are desired because they are non-yellowing. Other initiators which may maintain the desired water-white and water-clear appearance of the present hydrogels also are desired. Additional examples of suitable initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, tutylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), actophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropylthioxanthone), benzyl 2-ethyl anthraquinone, methylbenzoyl formate, 2-hydroxy-2-methyl-1-phenylpropane-1-one, 2-hydroxy-4'-isopropyl-2-methyl propiophenone, α-hydroxy ketone, tetramethyl thiuram monosulfide, allyl diazonium salt, and combinations of camphorquinone and ethyl 4-(N, N-dimethylamino)benzoate. Other suitable initiators may be found in, for example, Berner, et al., "Photo Initiators—An Overview", J. Radiation Curing (April 1979), pp. 2–9.

Although only one initiator is necessary, the hydrogel may contain one or more second initiators. The one or more second initiators can be photo or chemical initiators.

Where there is only one initiator, the amount of initiator is desirably within the range of about 0.01 to about 5% by weight of the hydrogel precursor, more desirably, within the range of about 0.05 to about 2% by weight of the hydrogel precursor and, even more desirably, within the range of about 0.1 to about 0.5% by weight of the hydrogel precursor. Where one or more second initiators are present, the amount of one or more second initiators is desirably within the range of about 0.01 to about 5% by weight of the hydrogel precursor, and more desirably within the range of about 0.05 to about 2% by weight of the hydrogel precursor and, even more desirably, within the range of about 0.1 to about 0.5% by weight of the hydrogel precursor. However, where multiple initiators are present, it is generally desirable that the combined amount of the initiators be about 5% or less by weight of the hydrogel precursor, and more desirably within the range of about 0.02 to about 5% by weight of the hydrogel precursor.

UV curing parameters to achieve desired polymer properties are well known to those skilled in the art. A photo initiator for the present purposes tends to operate by absorbing select wavelengths of UV to produce radical initiating species to induce monomer polymerization. The wavelengths and curing area set the style of UV bulb used in the curing process. Inhibition of polymerization due to dissolved oxygen, monomer inhibitors, or other radical scavenging moieties may be overcome by changing the power, by pulsing, and/or by using initiator accelerators.

It will be appreciated that each photo initiator is responsive to a specific or narrow wavelength range of UV light. At least one aspect of the present invention takes advantage of this property and incorporates two or more photo initiators in a hydrogel precursor. The addition of more than one initiator in a hydrogel precursor allows for a broader range of the energy or range of wavelengths emitted by a UV source to be utilized. The utilization of multiple initiators can further reduce solubility limit concerns and related compatibility concerns, as more efficient polymerization may be able to be achieved with two initiators present in a hydrogel precursor than with either of the initiators used alone at the same overall initiator concentration.

While the use of solubilizers is contemplated so as to alleviate solubility concerns, it is also believed that the inclusion of multiple initiators which may be present at levels which independently would have been insufficient to obtain the desired polymerization can enable the use of additional initiators whose solubility limits in hydrogel precursors effectively precluded their use previously.

The synergistic effect of initiators has not been previously identified or exhibited in previous hydrogels which incorporated one photo initiator, if any initiator at all. It is further believed that the inclusion of initiators having different rates of initiation and/or the inclusion of initiators which begin initiation of polymerization of the monomer at different times relative to each other (such as that which may be experienced by multiple initiators (e.g., a thermally activated chemical initiator (TACI) and a photo initiator)) contributes to a higher yielding polymerization. That is, for example, where two photo initiators are included, one may have a lower UV wavelength trigger and may be more energetic (providing for a faster rate of initiation and reaction) than the other initiator which is triggered by a higher UV wavelength or range. The faster initiator may also die or be consumed faster than the other. It is contemplated that it may be advantageous to have polymerization occur at different rates and/or at a mixed rate which may not be obtainable with one initiator or with an initiator which is suitable for a particular hydrogel precursor. An example of initiators which are not triggered or activated simultaneously, may be found in the present invention where a photo initiator and a TACI are in a hydrogel precursor, and the photo initiator is triggered by a UV source and reacts with the monomers in the precursor so as to generate heat to trigger the TACI.

While numerous combinations and variations of initiators are possible, it is believed that the combination of multiple initiators provides more favorable kinetics which afford a higher probability of more extensive polymerization of the monomer and/or other monomeric residues.

Of course, if desired or necessary, the multiple initiators also could be present at elevated solubility levels. In either instance, the inclusion of multiple initiators can result in a more completely polymerized hydrogel.

It is a further discovery of the present invention that a TACI may be included to take advantage of the benefits of multiple initiator polymerization. As some heat is necessary to trigger a TACI, it is contemplated that a TACI will generally be included only where heat will be present in or produced in the hydrogel precursor in a sufficient amount to trigger the TACI. As radical polymerization reactions induced by photo initiators are known to be exothermic and thus to generate heat in response to UV exposure, at least one aspect of the present invention is directed to the inclusion of a TACI in a hydrogel precursor where a photo initiator is also present so as to allow the TACI to take advantage of the heat generated by the radical polymerization reaction induced by a photo initiator. It is also contemplated that a TACI can be included where multiple photo initiators are present. The presence of multiple photo initiators provides for the potential benefits of multiple initiators discussed above yet also provides for the triggering of a TACI where the heat generated by one photo initiator may be insufficient to trigger or fully trigger the TACI (depending on the photo initiators and the TACI involved), whereby the TACI can further promote or complete the polymerization of the functional monomer and other monomeric residues in a hydrogel precursor. Multiple TACIs are also contemplated.

Nowhere in the literature of prior art or clinical experience has there been any report or knowledge of utilizing the combination of one or more photo initiators and a TACI in order to obtain the more complete polymerization of a hydrogel precursor, thereby leading to a more stable, less malodorous, and/or less skin irritating hydrogel.

As is also noted above, cross-linking agents are desirably used to cross-link the present hydrogels. Examples of multi-functional cross-linking agents which may be used include, for example, methylene-bis-acrylamide and diethylene glycol diacrylate which are both commercially available from Polysciences, Inc., Warrington, Pa. Additional examples of cross-linking agents which may be acceptable for use in the present invention include: poly(ethylene glycol) diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other multifunctional polyacrylate and polymethacrylate crosslinkers.

The amount of cross-linking agent is desirably within the range of about 0.01 to about 2% by weight of the hydrogel precursor and, more desirably, within the range of about 0.05 to about 0.5% by weight of the hydrogel precursor.

We will now turn to specific exemplary embodiments of hydrogels of the present invention. A number of exemplary formulas are provided below. With the exception of Formula 1 which is provided as a control, each of Formulas 2–6 relate to at least one aspect of the present invention. In each of the Formulas, the starting materials were mixed in the order given below and placed under a Fusion Systems 600 Watt Continuous UV Lamp.

UV Curing equipment and process parameters: a F600S Ultra-violet Lamp System (Fusion UV Systems, Inc., Woburn, Mass.) was used at a dose of about 5.084 J/cm$^2$ Formula 1 (Control)

48.64% DI Water 47.13% Monomer (N,N-Dimethylaminoethyl acrylate ammonium DMS (available from Ciba Specialty Chemicals under the tradename AGEFLEX® FA1Q80DMS))

0.1% Photo initiator (IRGACURE® 184)

0.09% Cross-linking Agent (Methylene-Bis-Acrylamide (available from Aldrich)

2.11% Electrolyte (Aluminum Potassium Sulfate)

1.5% Buffer (Sodium hydroxide)
0.43% DMSO
Formula 2
33% DI Water
63.8% Monomer (AGEFLEX® FA1Q80DMS)
0.1% Photo initiator (IRGACURE® 184)
0.1% Photo initiator (IRGACURE® 2959)
0.2% Cross-linking Agent (Poly(ethylene glycol)-400-diacrylate (PEG 400 DA))
1% Electrolyte (Potassium Sulfate)
0.8% Buffer (Sodium hydroxide)
1% Solubilizer (Hydroxypropylβ-cyclodextrin)
Formula 3
35.78% DI Water
60.91% Monomer (AGEFLEX® FA1Q80DMS)
0.1% Photo initiator (IRGACURE® 184)
0.1% Photo initiator (IRGACURE® 2959)
0.1% Chemical initiator (Sodium metabisulfite)
0.2% Cross-linking Agent (PEG 400 DA))
1% Solubilizer (Hydroxypropyl β-cyclodextrin)
1% Electrolyte (Potassium Sulfate)
0.8% Buffer (Sodium hydroxide)
0.01% Coloring additive (FD&C Green #3)
Formula 4
31.79% DI Water
65% Monomer (AGEFLEX® FA1 Q80DMS)
0.1% Photo initiator (IRGACURE® 184)
0.1% Cross-linking Agent (Methylene-Bis-Acrylamide)
1% Electrolyte (Potassium Sulfate)
0.8% Buffer (Sodium hydroxide)
0.2% Aloe Vera gel
0.01% Coloring additive (FD&C Blue #1)
1% Solubilizer (Hydroxypropyl β-cyclodextrin)
Formula 5
34.6% DI Water
62% Monomer (AGEFLEX® FA1Q80DMS)
0.1% Photo initiator (IRGACURE® 184)
0.1% Photo initiator (IRGACURE® 2959)
0.2% Cross-linking Agent (PEG 400 DA)
1% Solubilizer (Hydroxypropyl β-cyclodextrin)
1% Electrolyte (Potassium Sulfate)
0.8% Buffer (Sodium hydroxide)
0.2% Aloe Vera gel
Formula 6
35.49% DI Water
61% Monomer (AGEFLEX® FA1Q80DMS)
0.1% Photo initiator (IRGACURE® 184)
0.1% Second initiator (IRGACURE® 2959)
0.1% Photo initiator (Sodium metabisulfite)
0.2% Cross-linking Agent (PEG 400 DS))
1% Solubilizer (Hydroxypropyl β-cyclodextrin)
1% Electrolyte (Potassium Sulfate)
0.8% Buffer (Sodium hydroxide)
0.2% Aloe Vera gel
0.01% Coloring additive (FD&C Green #3)

After being formed each of the hydrogels was tested for residual amounts of 1) quaternary acrylic monomer, 2) acrylic acid, and 3) methyl acrylate. The amounts of residual quaternary acrylic monomer, residual acrylic acid and residual methyl acrylate were each tested for by high pressure liquid chromatography (HPLC).

HPLC Method—AGEFLEX Quaternary Monomer

Approximately 1 gram of the hydrogel was placed into a microwave extraction liner. 10 ml of IPA was added. The liner was placed in a microwave extraction vessel and placed in the microwave oven. The extraction occurred under the following conditions:

| Extraction Conditions: | |
|---|---|
| System: | CEM MARSX Microwave 1200 watt extraction system |
| Power: | 100% |
| Solvent: | IPA |
| Ramp: | 1.0 min |
| Hold time: | 5 min/sample |
| Temp: | 80° C. |

Once extraction was complete HPLC analysis of AGEFLEX Quaternary Monomer was performed under the following conditions:

| | |
|---|---|
| System: | HP 110 Quaternary HPLC |
| Column: | Supelcosol LC-SCX (4.6 × 250 mm) Cat# 5-8997 |
| Mobile Phase: | 62% Acetonitrile/38% 0.14M Ammonium Formate |
| Flow rate: | 1.0 ml/min |
| Detector: | Agilent 1100 Series G1315A DAD at 210 nm, 20 Ref = 350 nm, 90 |
| Injection Vol: | 2 μl |
| Elution Time: | 7.9 min |

HPLC Method—Acrylic Acid and Methyl Acrlyate

Approximately 0.1 gm of the monomer was accurately weighed into a 10.0 ml volumetric flask. Isopropyl alcohol (IPA) was added to the flask before placing in an ultrasonic bath for dissolution. Once dissolved the flask was dissolve to volume with IPA. An aliquot of the solubilized monomer was filtered through a 0.45 μm PFTE membrane filter to make HPLC-ready.

Acrylic acid (Aldrich #14,723-0, 99%) stock standard was prepared in IPA at a concentration of 950 μg/ml. Four aliquots of 0.1, 0.5, 2.0 and 5.0 mls were taken from the stock standard and transferred to four 10.0 ml volumetric flasks to prepare working standards with a concentration of 10 to 480 μg/ml.

Methyl acrylate (Aldrich M2,730-1, 99%) stock standard was prepared in IPA at a concentration of 730 μg/ml. Four aliquots of 0.5, 1.0, 3.0 and 6.0 mls were taken from the stock standard and transferred to four 10.0 ml volumetric flasks to prepare working standards with a concentration of 36 to 440 μg/ml.

The HPLC analysis for Acrylic acid and Methyl acrlyate was performed under the following conditions:

| | |
|---|---|
| System: | HP 110 Quaternary HPLC |
| Column: | Phenomenex Synergi 4 μ Polar-RP 80 Å (4.6 × 75 mm) |
| Mobile Phase: | 0.1% Formic acid/Ethanol/Methanol (96/3/1) |
| Flow rate: | 1.5 ml/min |
| Detector: | HP 1100 Diode Array at 210 nm, 4 Ref = 350 nm, 90 |
| Injection Vol: | 2 μl |
| Elution Time: | Acrylic Acid - 1.3 min |
| | Methyl Acrylate - 3.6 min |

The results of those tests are shown in TABLE 1 below.

TABLE 1

|  | % Residual Quaternary Monomer | % Residual Acrylic Acid | % Residual Methyl Acrylate |
|---|---|---|---|
| Formula 1 | 1.53 | 0.51 | 0.05 |
| Formula 2 | 1.31 | 0.19 | 0.06 |
| Formula 3 | 1.45 | 0.17 | 0.05 |
| Formula 4 | 1.92 | 0.13 | 0.06 |
| Formula 5 | 1.74 | 0.15 | 0.05 |
| Formula 6 | 1.54 | 0.17 | 0.06 |

As can be seen from TABLE 1, the hydrogels formed from the precursor formulas set forth in Formulas 2–6 demonstrate on overall reduction in monomeric residues. Most notably there is a significant decrease in the percentage of residual acrylic acid in the hydrogel. In some instances there is also shown a reduction in the percentages of residual quaternary monomer and/or residual methyl acrylate. While the decrease in residual quaternary monomer and/or residual methyl acrylate is small or even non-existent in some instances, the overall decrease in monomeric residues is significant.

It will be appreciated that as acrylic acid is known to be a skin irritant as well as to put off an acrid odor, the resulting hydrogels of the present invention are significantly less malodorous and less irritating to the skin.

It is of note that the present invention further distinguishes itself from prior hydrogels which incorporated dimethyl sulfoxide (DMSO) as an organic solvent. While DMSO was believed to be an excellent vehicle to pass through the skin of a subject and was thought to have been able to carry water to the skin of the subject in order to provide a good electrical conductivity path, it also may carry irritating residues into the inner skin layers thus potentially resulting in a rash or other undesired bodily reaction.

The hydrogels of the present invention are able to withstand the high voltages and currents of defibrillation and cardiac pacing. The hydrogels of the present invention are particularly suited for use in electronic medical devices such as: sensing electrodes which are used for recording or monitoring (e.g., for electrocardiogram, electroencephalogram, or electromyogram); stimulation electrodes which are used to stimulate a subject (e.g., for transcutaneceous electrical nerve stimulation, for wound healing, for muscle stimulation (e.g., for physical therapy), for external pacing, for defibrillation); electro-surgical and/or ablation grounding electrodes; and electro-transport electrodes (e.g., for the iontophoresis or electrophoresis of drugs into a subject).

One problem with past such devices is that the hydrogels used were not chemically compatible with aluminum or stainless steel (the hydrogel would cause corrosion of such metal contacting it); or if the hydrogel did not corrode the metal, it did not pass standards testing for biocompatibility and electrical properties as developed by the Association for the Advancement of Medical Instrumentation (AAMI) and accepted by the American National Standards Institute. Therefore, prior acceptable hydrogel devices used tin electrodes or other metal electrodes. However, use of aluminum electrodes is desired because such electrodes are radiolucent and, therefore, do not interfere with radio assays of a subject which includes such an electrode whereas electrodes made of tin or other metals do interfere with such assays. The hydrogels of the present invention present a family of hydrogels which do not include chlorides, and which are, therefore, chemically compatible with aluminum and/or stainless steel electrodes contacting the hydrogel.

In summary, it has been discovered that the hydrogel precursors of the present invention provide for a hydrogel which provide for a reduction in odor and skin irritation to the patient as compared to prior hydrogels. The novel formulations provide the ability of using the hydrogel or devices incorporating the hydrogel (e.g., electrodes) for longer periods of time without concern or with reduced concern for skin irritation and/or malodor. The formulations of the present invention desirably provide or are directed to at least one of the following: a more efficient polymerization process, a synergistic initiation system (or at least one which has a synergistic effect) including UV-activated initiators (photoinitiator) and/or heat-activated initiators, a polymerizing monomer solution that includes solubilizing agents to improve the homogeneity of the polymerizing solution, complexing agents to lower the volatility of volatile compounds, and skin care ingredients that could protect skin against undesirable elements.

It should be noted that whereas various mechanisms have been put forth here to explain the discovery of the reduction in skin irritation and/or malodorous properties in connection with enhanced or more complete polymerization of the monomer and/or monomeric residue in the hydrogels of the present invention, the precise reasoning and/or mechanism of this skin irritation and/or malodor relieving process has not been totally clarified. For example, the role of hydrolysis of the hydrogel and/or the production of byproducts may play some role. The presence of residue in the monomer as received from the manufacturer and the subsequent reactions involving such monomeric residue may be additional contributory factors of significance. Although the precise origins of the skin irritation and odor relief have not been totally elucidated, nonetheless, this does not diminish a spectacular discovery which is pertinent to this invention, namely that enhanced polymerization and/or complexion of volatile molecules of hydrogel monomers dramatically relieves the malodorous and skin-toxic properties in hydrogels.

It should also be noted that while the above specific examples show particular desired embodiments of the present invention, substitution of the specific constituents of those examples with materials as disclosed herein and as are known in the art may be made without departing from the scope of the present invention. Thus, while different aspects of the present invention have been shown and described, various modifications may be made without departing from the scope of the present invention, and all such modifications and equivalents are intended to be covered.

We claim:

1. An electrically conductive hydrogel formed from a composition comprising:
    a monomer;
    an initiator;
    a cross-linking agent; and
    a solubilizer selected from the group consisting of cyclodextrin, cyclodextrin derivatives, and hydrotropes.

2. The electrically conductive hydrogel of claim 1 characterized in that the solubilizer allows for a higher initiator concentration to be solubilized in the composition; and such that the composition has a higher polymerizing potential than a similar composition without the solubilizer.

3. The electrically conductive hydrogel of claim 1 having a lower concentration of residual monomeric compounds present in the hydrogel than that of a similar hydrogel without the solubilizer.

4. The electrically conductive hydrogel of claim 1, wherein the solubilizer is selected from the group consisting of hydroxypropyl beta-cyclodextrin, gamma cyclodextrin, and methacryloyl cyolodextrin.

5. The electrically conductive hydrogel of claim 1, wherein the solubilizer comprises less than about 20% by weight of the composition.

6. The electrically conductive hydrogel of claim 1, wherein the composition further comprises a second initiator.

7. The electrically conductive hydrogel of claim 1, wherein the composistion further comprises a conductivity enhancer.

8. The electrically conductive hydrogel of claim 1, wherein the composition further comprises a buffer.

9. The electrically conductive hydrogel of claim 1, wherein the monomer comprises about 10% to about 80% by weight of the composition.

10. The electrically conductive hydrogel of claim 1, wherein the monomer comprises about 40% to about 75% by weight of the composition.

11. The electrically conductive hydrogel of claim 1, wherein the initiator comprises about 0.01% to about 2% by weight of the composition.

12. The electrically conductive hydrogel of claim 1, wherein the cross-linking agent comprises about 0.01% to about 2% by weight of the composition.

13. The electrically conductive hydrogel of claim 7, wherein the conductivity enhancer comprises less than about 5% by weight of the composition.

14. The electrically conductive hydrogel of claim 1, wherein the monomer is selected from the group consisting of N,N-Dimethylaminoethyl acrylate ammonium DMS, dimethyl amino ethyl methacrylate, acrylamido methyl propane sulfonic acid, and their salts.

15. The electrically conductive hydrogel of claim 1, wherein the initiator is a chemical or photo initiator.

16. The electrically conductive hydrogel of claim 1, wherein the initiator is a thermally activated chemical initiator.

17. The electrically conductive hydrogel of claim 16, wherein the thermally activated chemical initiator is selected from the group consisting of disulfide based, peroxide based, and persulfate based initiators.

18. The electrically conductive hydrogel of claim 16, wherein the thermally activated chemical initiator is sodium metabisulfite.

19. The electrically conductive hydrogel of claim 1, wherein the initiator is a hydrophobic initiator.

20. The electrically conductive hydrogel of claim 1, wherein the composition further comprises a skin health agent.

21. The electrically conductive hydrogel of claim 20, wherein the skin health agent is selected from aloe Vera, vitamin E, vitamin B, provitamin B, vitamin E acetate, and chitosan.

22. An electrically conductive hydrogel formed from a composition comprising:
an ionic monomer;
a first initiator;
a solubilizer; and
a cross-linking agent;
wherein the solubilizer is selected from the group consisting of cyclodextrin and cyclodextrin derivatives.

23. The electrically conductive hydrogel of claim 22, wherein the composition further comprises a conductivity enhancer.

24. The electrically conductive hydrogel of claim 23, wherein the conductivity enhancer is an electrolyte.

25. The electrically conductive hydrogel of claim 22, wherein the composition further comprises a buffer.

26. The electrically conductive hydrogel of claim 22, wherein the monomer comprises about 10% to about 80% by weight of the composition.

27. The electrically conductive hydrogel of claim 22, wherein the monomer comprises about 40% to about 75% by weight of the composition.

28. The electrically conductive hydrogel of claim 22, wherein the first initiator is a hydrophobic initiator.

29. An electrode comprising an electrically conductive adhesive hydrogel formed from a composition comprising:
a monomer;
a first initiator;
a solubilizer; and
a cross-linking agent.

30. The electrode of claim 29 characterized in that the solubilizer allows for a higher initiator concentration to be solubilized in the composition; and such that the composition has a higher polymerizing potential than a similar composition without the solubilizer.

31. The electrode of claim 29 having a lower concentration of residual monomeric compounds present in the hydrogel than that of a similar hydrogel without the solubilizer.

32. The electrode of claim 29, wherein the solubilizer comprises less than about 20% by weight of the composition.

33. The electrode of claim 29, wherein the solubilizer of the composition is selected from the group consisting of cyclodextrin, cyclodextrin derivatives, and hydrotropes.

34. The electrode of claim 29, wherein the solubilizer of the composition is selected from the group consisting of hydroxypropyl beta-cyclodextrin, gamma cyclodextrin, and methacryloyl cyclodextrin.

35. The electrode of claim 29, wherein the monomer comprises about 10% to about 80% by weight of the composition.

36. The electrode of claim 29, wherein the monomer of the composition is selected from the group consisting of N,N-Dimethylaminoethyl acrylate ammonium DMS, dimethyl amino ethyl methacrylate, acrylamido methyl propane sulfonic acid and their salts.

37. The electrode of claim 29, wherein the first initiator is a hydrophobic initiator.

38. The electrode of claim 29, wherein the composition further comprises a second initiator.

39. The electrically conductive hydrogel of claim 22, wherein the composition further comprises a second initiator.

* * * * *